US006234958B1

(12) United States Patent
Snoke et al.

(10) Patent No.: US 6,234,958 B1
(45) Date of Patent: May 22, 2001

(54) MEDICAL DEVICE INTRODUCTION SYSTEM INCLUDING MEDICAL INTRODUCER HAVING A PLURALITY OF ACCESS PORTS AND METHODS OF PERFORMING MEDICAL PROCEDURES WITH SAME

(75) Inventors: Phillip Jack Snoke, Atlanta; Randall J. Hasslinger, Alpharetta; Marcus E. Finch, Altanta; Michael J. Mark, Suwanee, all of GA (US)

(73) Assignee: Medical Access Systems, LLC, Atlanta, GA (US)

( * ) Notice: Subject to any disclaimer, the term of this patent is extended or adjusted under 35 U.S.C. 154(b) by 0 days.

(21) Appl. No.: 09/201,016

(22) Filed: Nov. 30, 1998

(51) Int. Cl.$^7$ ..................................................... A61B 1/00

(52) U.S. Cl. ........................... 600/114; 600/106; 600/115

(58) Field of Search ..................................... 600/102, 104, 600/106, 113, 114, 115, 116, 130, 135, 136, 137, 153, 154; 604/28, 95, 523, 912, 915

(56) References Cited

U.S. PATENT DOCUMENTS

| | | | |
|---|---|---|---|
| 3,978,863 | * | 9/1976 | Fettel et al. ........................... 606/194 |
| 4,245,624 | * | 1/1981 | Komiya ................................. 600/106 |
| 4,538,594 | * | 9/1985 | Boebel et al. ........................ 600/102 |

(List continued on next page.)

FOREIGN PATENT DOCUMENTS

| | | | |
|---|---|---|---|
| 95/08357 | 3/1995 | (WO) | ............................................. 3/0 |
| 97/36536 | 10/1997 | (WO) | ........................................ 1/307 |
| 98/24501 | 6/1998 | (WO) | .......................................... 25/0 |

OTHER PUBLICATIONS

Ackrad Laboratories, Inc., *Bibliography of Hysterosonography/Sonohysterography Scientific Papers*, pp. 1–6.
Fertility and Sterility, *A New System for Fallopian Tube Sperm Perfusion Leads to Pregnancy Rates Twice as High as Standard Intrauterine Insemination*, vol. 64, No. 3, Sep. 1995.
Ethicon Endo–Surgery, Inc., ENDOPATH Dilating Tip Trocar, Brochure No. ENDO336, 1996.
C.C.D. International, Medical Devices Catalog, 1998.
Ackrad Laboratories, Inc., Tampa Catheter Set for Hysterosonography, May 1997.
Ackrad Laboratories, Inc., H/S Elliptosphere Catheter Set, Feb. 1998.
Soprane Technologie Chirurgicale, Fertiloscopy Introducer, France.

(List continued on next page.)

*Primary Examiner*—John P. Leubecker
(74) *Attorney, Agent, or Firm*—Allen, Dyer, Doppelt, Milbrath & Gilchrist, P.A.

(57) ABSTRACT

A medical device introduction system, a medical introducer, and related methods are provided. The medical device introduction system preferably includes a medical introducer having an introducer body and a plurality of lumen formed therein, an imaging device positioned in a predetermined one of the plurality of lumen of the medical introducer so that the imaging device is separately controllable independent of the medical introducer, and a separate steerable working channel device positioned in at least one other of the plurality of lumen of the medical introducer so that the separate steerable working channel device and the imaging device are separately controllable by a user thereof independent of each other. The separate steerable working channel device preferably includes an elongate tube portion having at least one lumen formed therein which defines the working channel and steering means associated with the elongate tube portion for steering the elongate tube portion.

86 Claims, 9 Drawing Sheets

U.S. PATENT DOCUMENTS

| | | | |
|---|---|---|---|
| 4,577,621 | * | 3/1986 | Patel ............................ 600/114 |
| 4,588,398 | | 5/1986 | Daugherty et al. . |
| 4,616,631 | * | 10/1986 | Takahashi ....................... 600/139 |
| 4,737,142 | * | 4/1988 | Heckele .......................... 604/95 |
| 4,756,303 | | 7/1988 | Kawashima et al. . |
| 4,813,425 | | 3/1989 | Malis . |
| 4,878,898 | * | 11/1989 | Griffin et al. .................... 604/101 |
| 4,956,486 | | 9/1990 | Davis . |
| 4,957,486 | * | 9/1990 | Davis ............................. 604/96 |
| 4,972,827 | * | 11/1990 | Kishi et al. ..................... 600/114 |
| 4,983,169 | | 1/1991 | Furnkawa . |
| 4,984,563 | * | 1/1991 | Renaud ........................... 600/108 |
| 5,025,778 | | 6/1991 | Silverstein et al. . |
| 5,071,429 | * | 12/1991 | Pinchuk et al. ................. 606/192 |
| 5,078,681 | * | 1/1992 | Kawashima ..................... 606/198 |
| 5,083,549 | | 1/1992 | Cho . |
| 5,106,368 | | 4/1992 | Uldall et al. . |
| 5,152,277 | * | 10/1992 | Honda et al. ................... 600/116 |
| 5,251,613 | * | 10/1993 | Adair ............................. 600/109 |
| 5,261,889 | * | 11/1993 | Laine et al. ..................... 604/164 |
| 5,331,947 | * | 7/1994 | Shturman ....................... 600/115 |
| 5,342,299 | | 8/1994 | Snoke et al. . |
| 5,354,266 | | 10/1994 | Snoke . |
| 5,360,389 | * | 11/1994 | Chenette ......................... 600/34 |
| 5,377,668 | | 1/1995 | Ehmsen et al. . |
| 5,386,817 | * | 2/1995 | Jones ............................. 600/104 |
| 5,391,147 | | 2/1995 | Imran et al. . |
| 5,395,328 | | 3/1995 | Ockuly et al. . |
| 5,395,329 | | 3/1995 | Fleischhacker et al. . |
| 5,402,768 | | 4/1995 | Adair . |
| 5,409,469 | | 4/1995 | Schaerf . |
| 5,409,483 | | 4/1995 | Campbell et al. . |
| 5,419,312 | | 5/1995 | Arenberg et al. . |
| 5,437,636 | | 8/1995 | Snoke et al. . |
| 5,443,454 | | 8/1995 | Tanabe et al. . |
| 5,460,167 | | 10/1995 | Yabe et al. . |
| 5,472,419 | * | 12/1995 | Bacich ........................... 604/515 |
| 5,483,951 | | 1/1996 | Frassica et al. . |
| 5,484,407 | | 1/1996 | Osypka . |
| 5,486,154 | | 1/1996 | Kelleher . |
| 5,488,960 | | 2/1996 | Toner . |
| 5,503,616 | | 4/1996 | Jones . |
| 5,507,725 | | 4/1996 | Savage et al. . |
| 5,531,687 | | 7/1996 | Snoke et al. . |
| 5,533,967 | | 7/1996 | Imran . |
| 5,542,937 | | 8/1996 | Chee et al. . |
| 5,643,175 | * | 7/1997 | Adair ............................. 600/133 |
| 5,688,246 | | 11/1997 | Waitz et al. . |
| 5,749,889 | | 5/1998 | Bacich et al. . |
| 5,755,702 | | 5/1998 | Hillstead et al. . |
| 5,772,628 | | 6/1998 | Bacich et al. . |
| 5,935,098 | * | 8/1999 | Blaisdell et al. ................ 604/55 |
| 5,961,444 | * | 10/1999 | Thompson ....................... 600/33 |
| 6,010,448 | * | 1/2000 | Thompson ....................... 600/34 |
| 6,013,024 | * | 1/2000 | Mitsuda et al. ................. 600/146 |
| 6,027,499 | * | 2/2000 | Johnston et al. ................ 606/22 |

OTHER PUBLICATIONS

Fertility and Sterility, *Prospective Randomized Study of Utero–Tubal Insemination (UTI) Versus Conventional intrauterine Insemination (IUI), p. 939;* The Impact of the Woman's Age . . ., p. 940; High Delivery Rate After Transfer of A Maximum of Three Fresh Embryos and Freezing at the Pronucleate Stage: Safety and Ethical Requirements are Positively Challenged, p. 941.

acog Technical Bulletin, Hysteroscopy, No. 191, Apr. 1994.

OBG Management, Micro endoscopy Moves Into the Office, Jan. 1997.

BEI Gynecology Products, Office Hysteroscopy with the Corson Hysteroscopy System, Stephen L. Corson, M.D., May 19, 1998.

BEI Gynecology Products, Office Sonohysterogrphy, Michael L. Nimaroff, M.D., May 19, 1998.

Biophotonics International, Endoscopy: Gain Without Pain—Endoscopes Provide Minimally Invasive Alternatives, Barbara Grant, Jul./Aug. 1997.

Circon, 1997 Complete Product Catalog.

Obstetrics & Gynecology, Office Hysteroscopy and Suction Curettage: Can we Eliminate the Hospital Diagnostic Dilatation and Curettage?, Milton H. Goldrath, MD, and Alfred L. Sherman, MD, pp. 220–225.

Obstetrics & Gynecology, Hysteroscopy with Selective Endometrial Sampling Compared with D&C for Abnormal Uterine Bleeding: The Value of a Negative Hysteroscopic View, Franklin D. Loffer, MD, FACOG, pp. 16, 17.

Obstetrics & Gynecology, Hysteroscopic Evaluation of Patients with Abnormal Uterine Bleeding, Rafael F. Valle, MD, FACS, p. 521.

\* cited by examiner

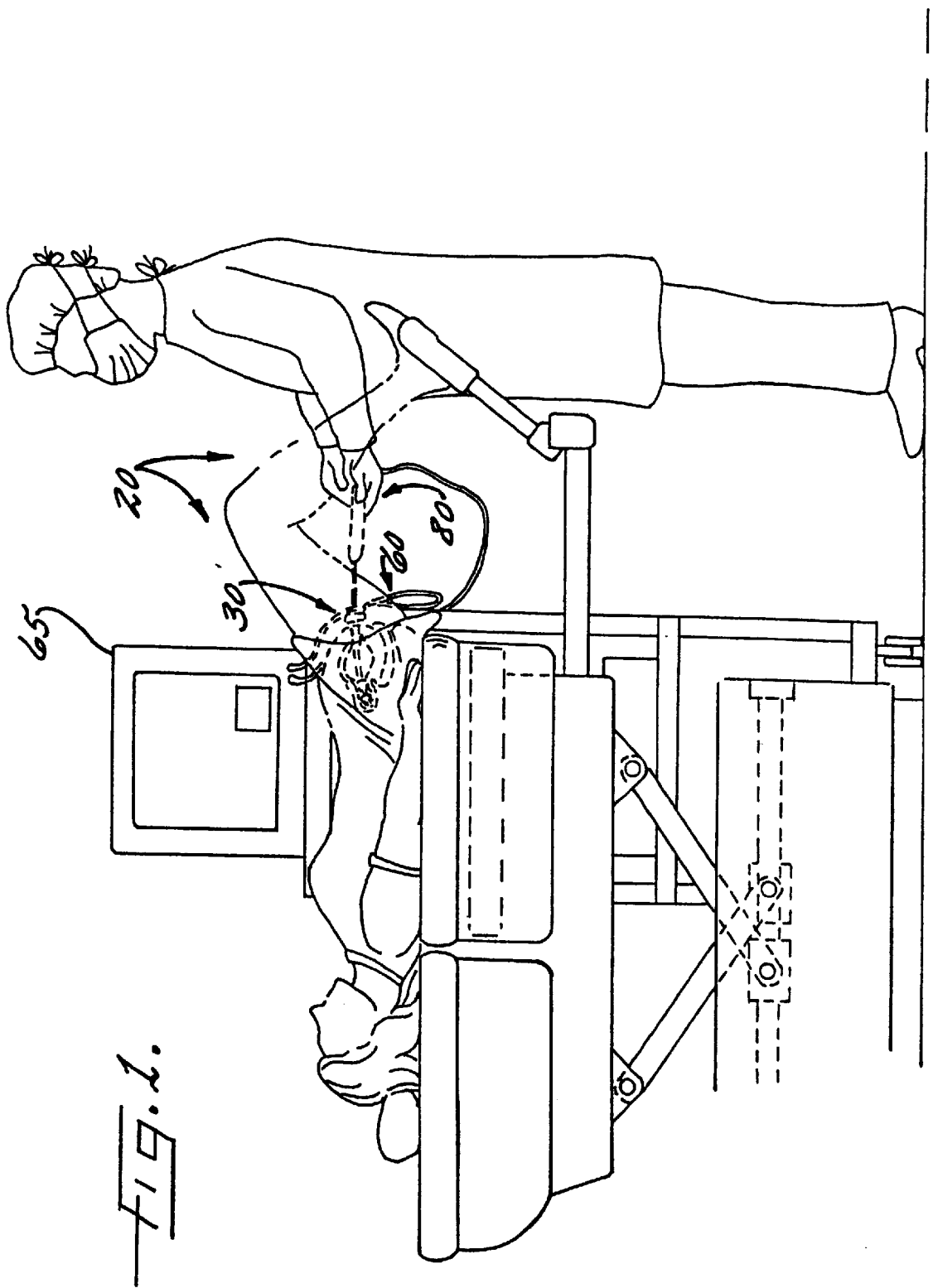

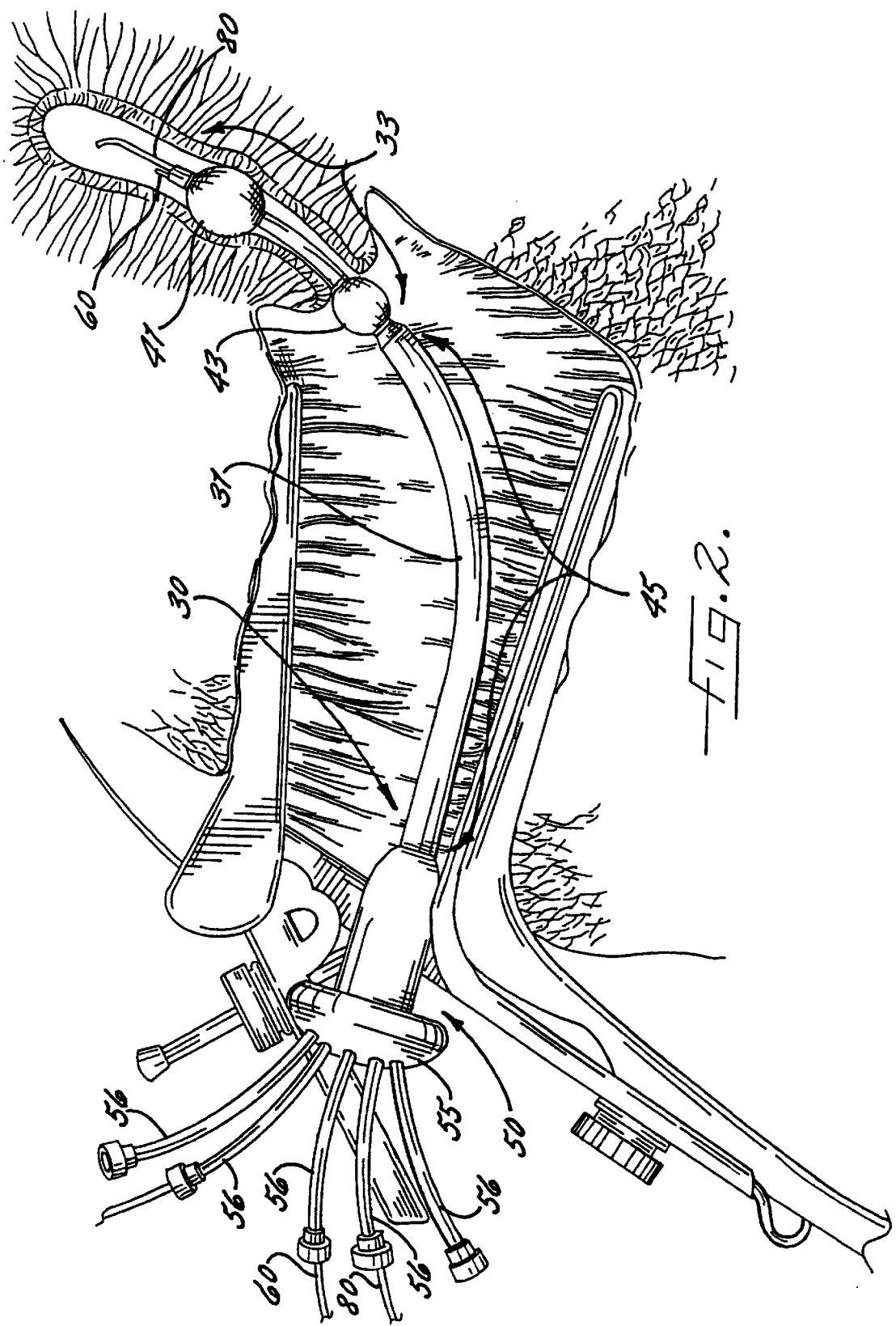

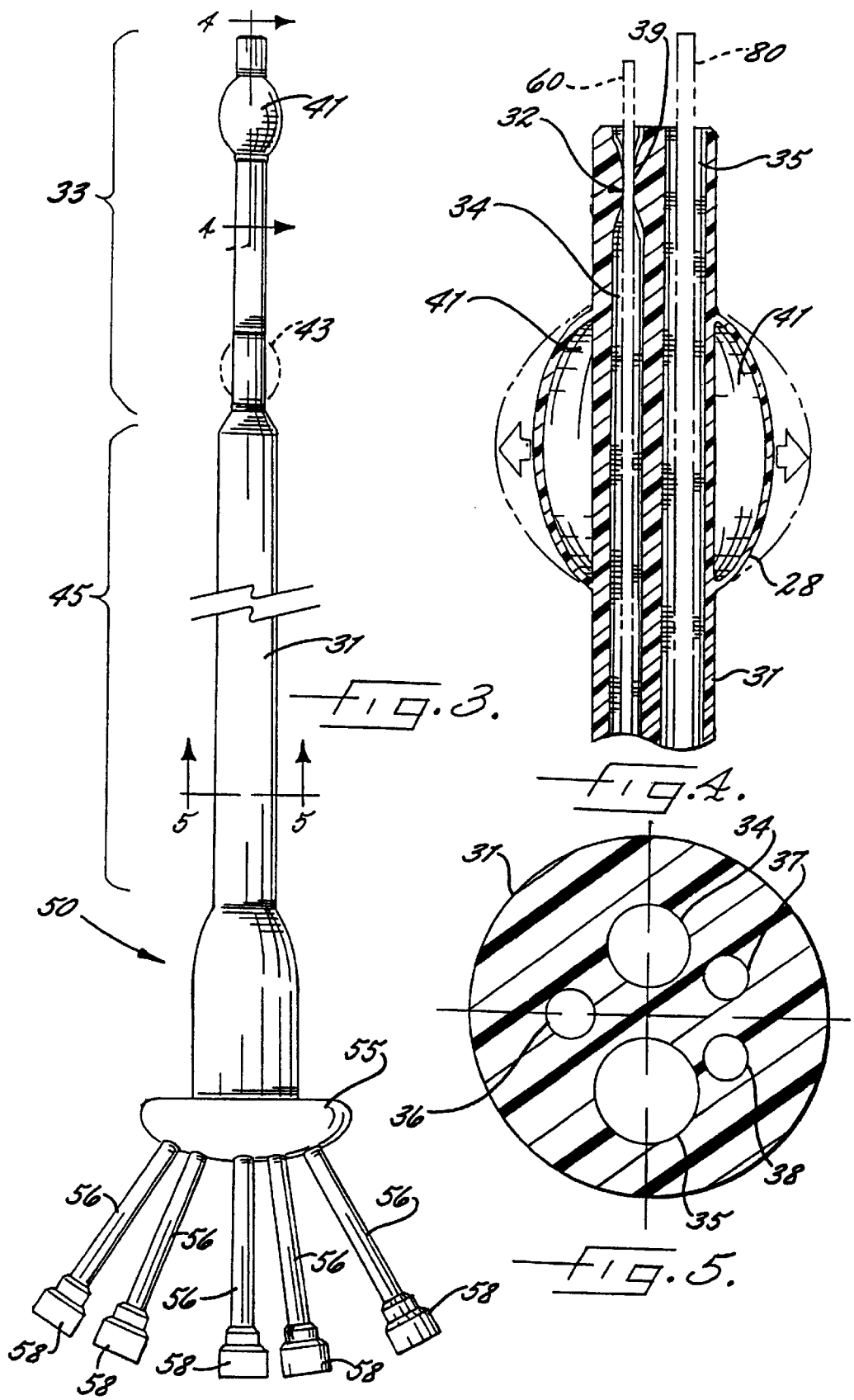

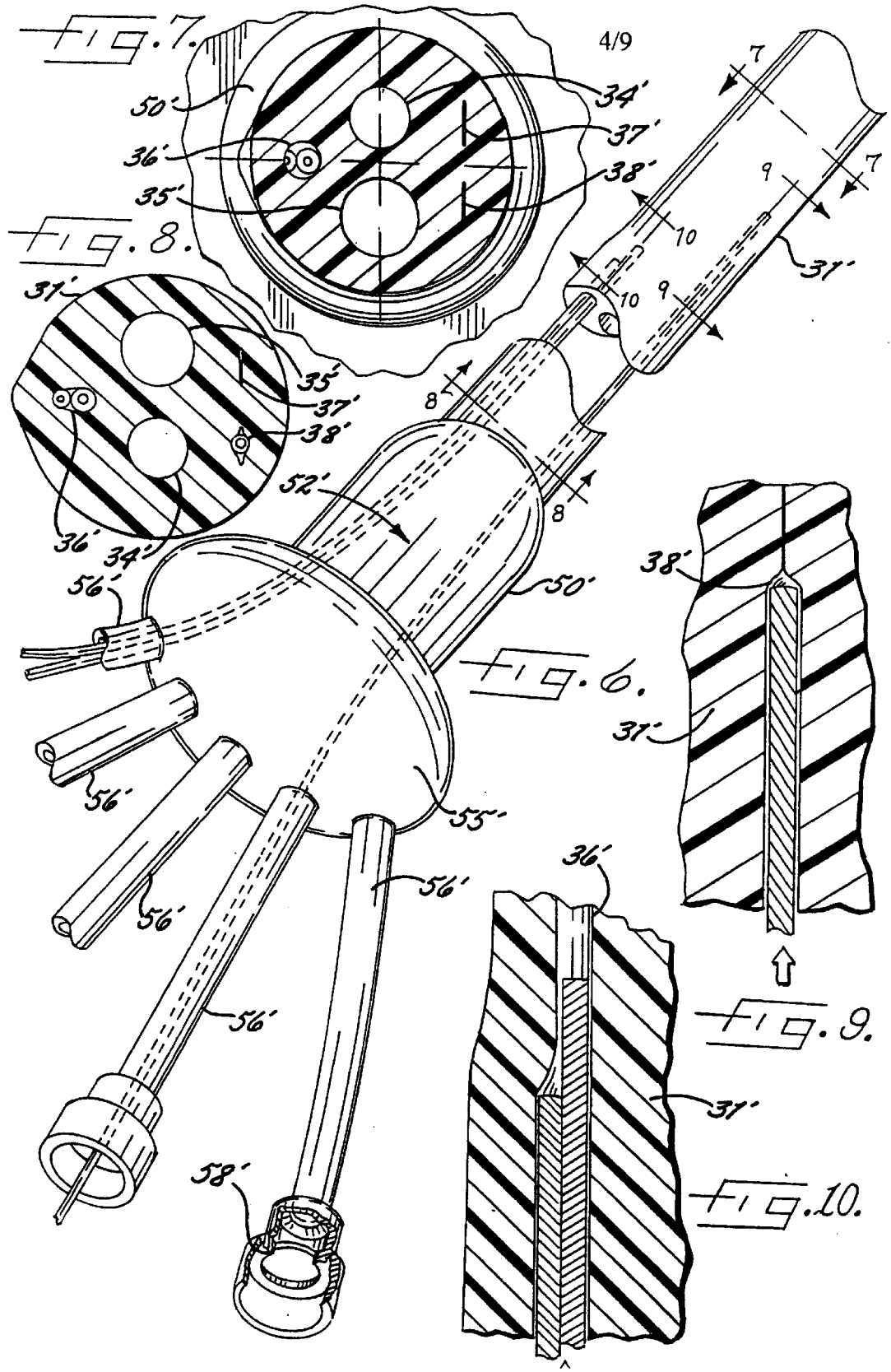

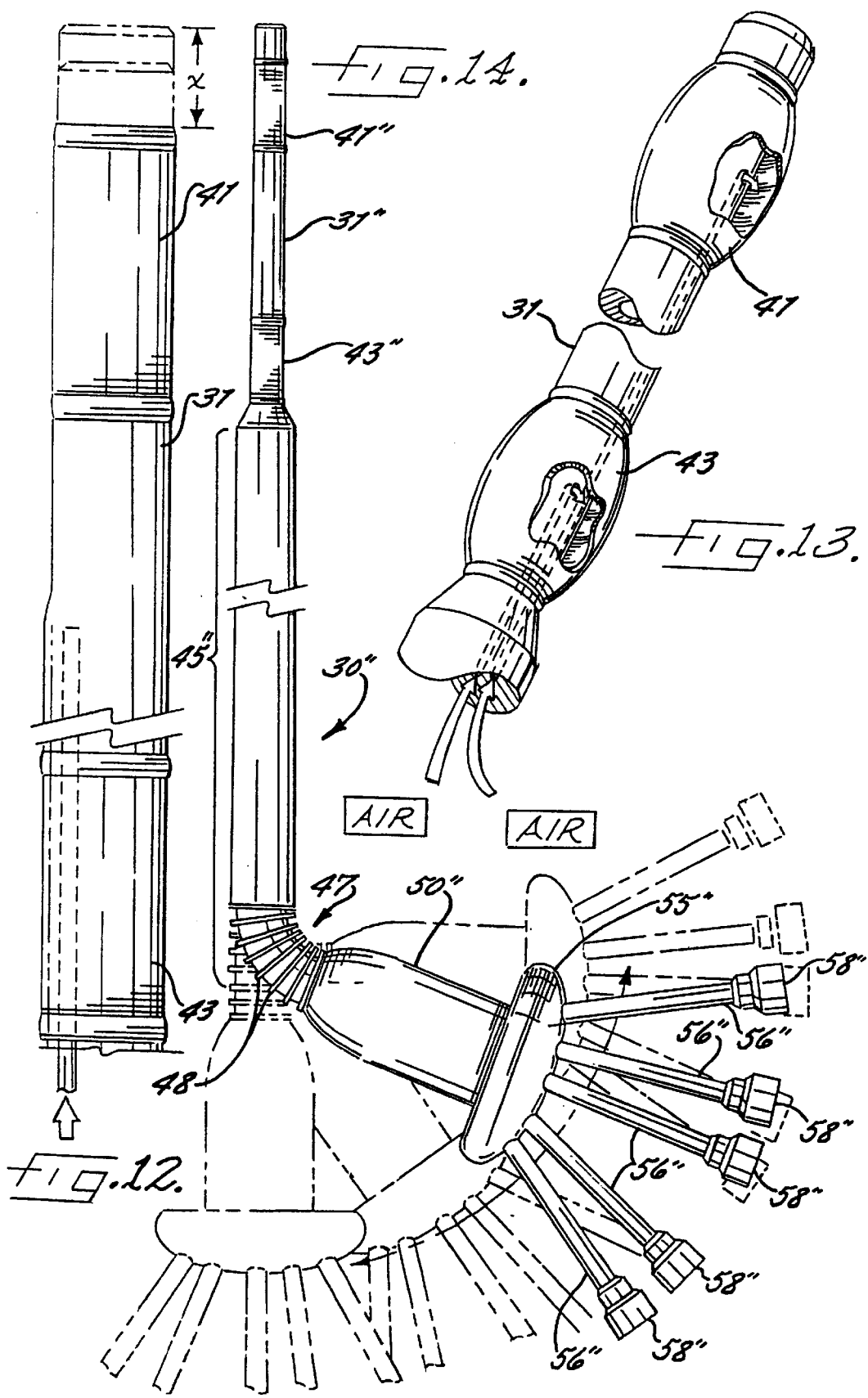

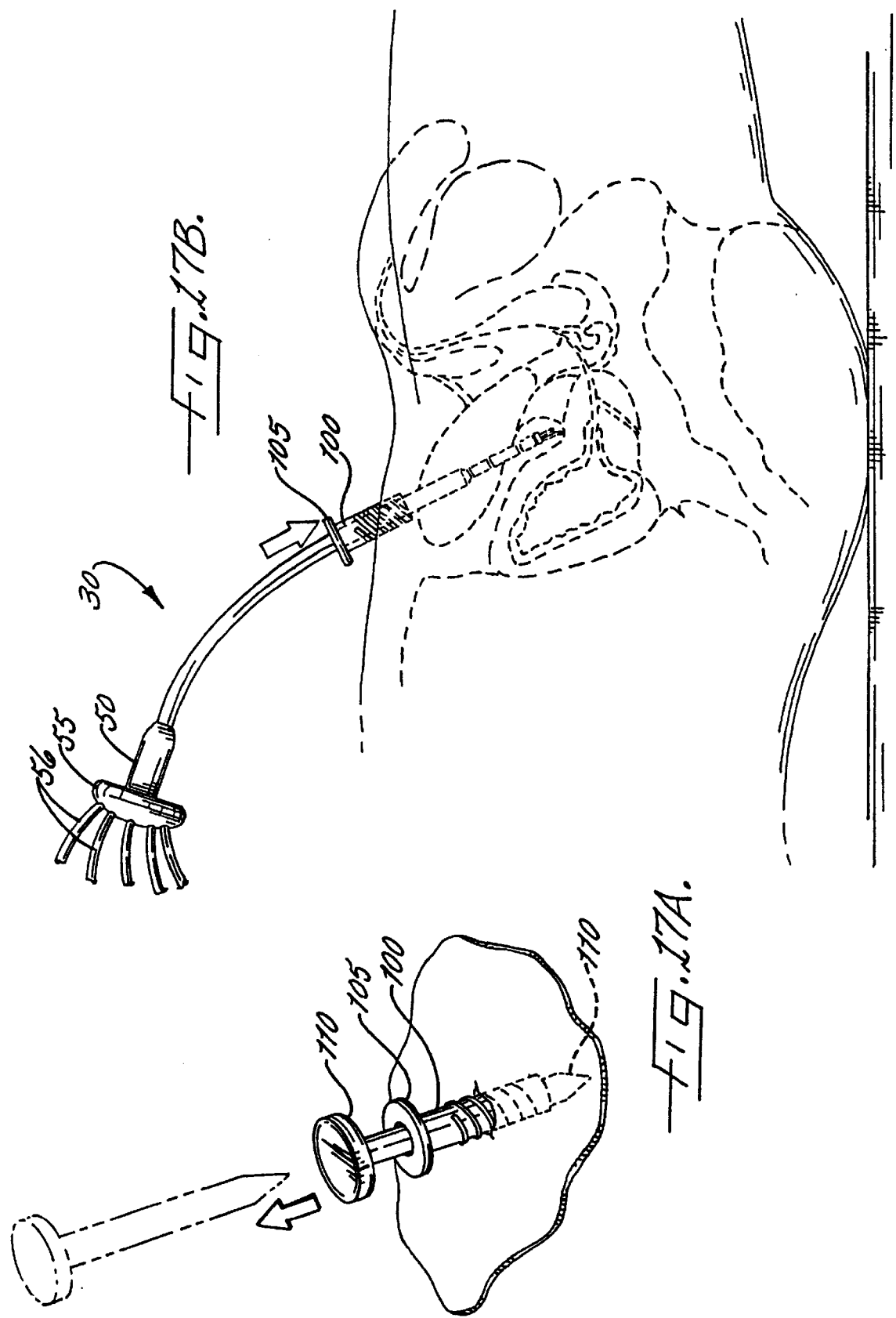

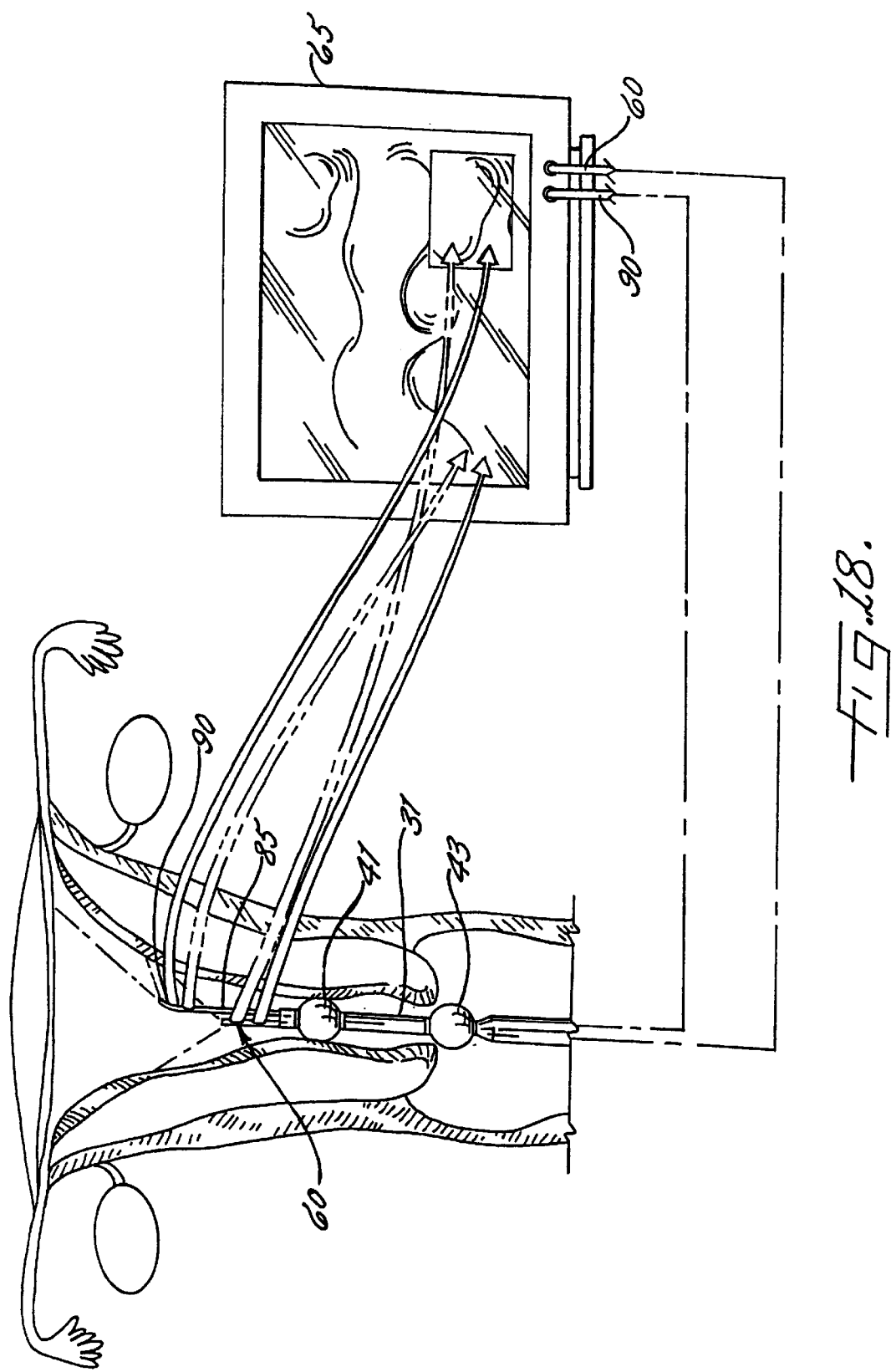

MEDICAL DEVICE INTRODUCTION SYSTEM INCLUDING MEDICAL INTRODUCER HAVING A PLURALITY OF ACCESS PORTS AND METHODS OF PERFORMING MEDICAL PROCEDURES WITH SAME

FIELD OF THE INVENTION

The present invention relates to the field of medical devices used in surgical operations and, more particularly, to medical devices and methods for introducing scopes, instruments, and/or fluids into a body cavity.

BACKGROUND OF THE INVENTION

Over the past few years, medical procedures have advanced to stages where less and less invasive or minimally invasive surgeries, diagnostic procedures, exploratory procedures, or other medical procedures have been desired and demanded both by patients, physicians, and various medical industry administrators. To accomplish these desires and demands, various medical devices and instrumentation has been developed such as cannulas or microcannulas, various catheter devices including steerable catheters, micro-surgical instrumentation and implants, medical introducers, fiber optic scopes and other imaging devices, and other endoscopic related devices.

In situations where minimally invasive procedures are being used, space within an opening, a cavity, a passageway, or a vessel of a patient's body becomes more and more constrained. Conventionally, a medical introducer is often used during a surgical or other medical procedure. An example of a hemostatic sheath introducer having a single lumen formed therein can be seen in U.S. Pat. No. 5,755,702 by Hillstead et al. titled "Adjustable Angular Sheath Introducer" which allows a main body lumen thereof to be at a different angle than a rotating section lumen. Even with the use of a single lumen medical introducer such as shown and described in U.S. Pat. No. 5,755,702, operating within tight or small spaces with a plurality of medical devices, such as instruments, scopes, fluids, catheters, implants, and the like, becomes difficult to manage by physicians and medical assistants. This is especially true where a single physician wants to perform a procedure in his office to reduce or prevent the need(s) for hospitalization.

Additionally, when performing a procedure with a plurality of medical devices, positioning, controlling, manipulating, and handling the various medical devices during the procedure can prevent physicians from performing as well as capable. In other words, the construction and design of the medical device becomes a system constraint, e.g., reduces or inhibits system flexibility, for the physician. For example, such constraints can require physicians to perform an exploratory procedure, a diagnostic procedure, and/or an actual surgical operation as two, three, or more different patient visits. To respond to some of these problems, various catheters and endoscopic devices have been developed which attempt to perform an "all-in-one" type function or which attempt to combine steering and other functions. Some examples of such attempts can be seen in U.S. Pat. No. 5,083,549 by Cho et al. titled "Endoscope With Tapered Shaft," U.S. Pat. No. 5,484,407 by Osypka titled "Catheter With Steerable Distal End," U.S. Pat. No. 5,772,628 by Bacich et al. titled "Surgical Access Device And Method Of Construction Same," U.S. Pat. No. 5,488,960 by Toner titled "Coronary Sinus Catheter Introducer System," U.S. Pat. No. 5,377,668 by Ehmsen et al. '668 titled Apparatus And Method For Endoscopic Diagnostics And Therapy," U.S. Pat. No. 5,443,454 by Tanabe et al. titled Catheter For Embolectomy," U.S. Pat. No. 5,342,299 by Snoke et al. titled "Steerable Catheter," and U.S. Pat. No. 5,354,266 by Snoke titled "Method Of Epidural Surgery."

One of the basic problems with these prior attempts, however, has been that by bundling too many features into a single medical device makes the device complex to manufacture and handle, expensive, and relatively large within a confined space. Also, when performing a procedure, the physician is often still limited by the devices capabilities, and if the physician attempts a procedure using additional devices, similar problems related to space and degrees of freedom arise again. In other words, the physical and structural constraints of the device can severely limit the physicians abilities to view, move around within the space, transition between procedures, and perform additional procedural function.

SUMMARY OF THE INVENTION

With the foregoing in mind, the present invention advantageously provides a medical device introduction system, a medical introducer, and associated methods which provide physician flexibility and increase the degrees of freedom for physicians during various medical procedures. The present invention also provides a simplified medical device introduction system and associated methods which allow an imaging device to be separably and independently controlled from a steerable working channel device, as well as from a medical introducer itself, and thereby enhance viewing within a portion of a body. The present invention additionally provides a medical device introduction system and associated methods which have flexible uses for various medical procedures so that more than one procedure can be performed during a single invasive event and thereby reduces the number of invasive events necessary to improve a patient's health. The present invention also provides a medical device introduction system and associated methods which enhances visibility by physicians or other health care professionals within a portion of a patient's body during a medical procedure. The present invention further provides a medical introducer which pivots to various positions to enhance medical procedure approaches and thereby expands the uses of the medical introducer. The present invention still further provides a medical introducer with expandable lumen so that the overall size or outside diameter of the introducer can be reduced for insertion during selected procedures and then increase if desired when additional medical devices or fluid are positioned therein to thereby reduce trauma to patients during multiple procedures.

More particularly, the present invention provides a medical device introduction system which preferably includes a medical introducer having an introducer body and a plurality of lumen formed therein, an imaging device positioned in a predetermined one of the plurality of lumen of the medical introducer so that the imaging device is separately controllable independent of the medical introducer, and a separate steerable working channel device positioned in at least one other of the plurality of lumen of the medical introducer so that the separate steerable working channel device and the imaging device are separately controllable by a user thereof independent of each other. The separate steerable working channel device is preferably provided by a separate multiple lumen device which includes an elongate tube portion having at least one lumen formed therein which defines the working channel and steering means associated with the elongate tube portion for steering the elongate tube portion.

A medical introducer for introducing medical devices therethrough and into a portion of a body according to the present invention preferably includes an introducer body, a plurality of lumen formed in the introducer body, and imaging device position maintaining means associated with at least an inner surface of a predetermined one of the plurality of lumen for maintaining a rotational position of a distal end portion of an imaging device when positioned within the predetermined one of the plurality of lumen.

An alternative embodiment of a medical introducer for introducing medical devices therethrough and into a portion of a patient's body according to the present invention preferably includes an introducer body including at least one inflatable portion associated with an outer surface of a predetermined distal end portion thereof for inflating the outer surface of the predetermined distal end portion from a collapsed to an enlarged position and a plurality of lumen formed therein. At least one of the plurality of lumen advantageously transitions from a smaller inside diameter in a distal end portion of the introducer body to a larger inside diameter in a medial portion of the introducer body to thereby allow tissue such as removed during surgical procedures to more readily pass therethrough.

The present invention also provides methods of performing a medical procedure. A method preferably includes inserting an imaging device through a medical introducer positioned within a portion of a body of a patient, positioning the imaging device to produce an image from within the portion of the patient's body, inserting a steerable working channel device through the same medical introducer, and controlling the steering of the steerable working channel separately and independently from the positioning of the imaging device.

Another method preferably includes positioning an imaging device through a first lumen of a medical introducer positioned within a uterine cavity of a body of a patient to thereby produce an image from within the uterine cavity, inserting a steerable working channel device through a second lumen of the same medical introducer, and inserting at least one of the following through the steerable working channel device when inserted within the uterine cavity: at least one gamete, at least one sperm, at least one egg, at least one embryo, or at least one blastocyst.

Yet another method of performing a medical procedure preferably includes inserting an endoscopic device, such as preferably provided by a cannula, into a portion of a patient's body, inserting a medical introducer having a plurality of lumen extending therethrough into the endoscopic device, inserting a steerable working channel device through one of the plurality of lumen of the same medical introducer, and controlling the steering of the steerable working channel.

The present invention also includes a method of viewing within a portion of a patient's body. The method preferably includes inserting an imaging device through one of a plurality of lumen of a medical introducer positioned within a portion of a patient's body, moving the imaging device to a selected position, maintaining the position of the imaging device in the selected position by use of the medical introducer and without the necessity of a user thereof manually maintaining the position, producing an image from within the portion of the patient's body, inserting a steerable working channel device through another one of the plurality of lumen of the same medical introducer, and controlling the steering of the steerable working channel without moving the position of the imaging device.

BRIEF DESCRIPTION OF THE DRAWINGS

Some of the features, advantages, and benefits of the present invention have been stated above. Others, however, also will become apparent as the description proceeds when taken in conjunction with the accompanying drawings in which:

FIG. 1 is an environmental view of a medical device introduction system being used during a medical procedure according to the present invention;

FIG. 2 is an enlarged perspective view of a medical introducer of a medical device introduction system being positioned in a uterine cavity of a female patient during a medical procedure according to the present invention;

FIG. 3 is a top plan view of a medical introducer having a plurality of access ports of a medical device introduction system according to the present invention;

FIG. 4 is a longitudinal sectional view of a medical introducer of a medical device introduction system taken along line 4—4 of FIG. 3 according to the present invention;

FIG. 5 is an enlarged transverse sectional view of a medical introducer of a medical device introduction system taken along line 5—5 of FIG. 3 according to the present invention;

FIG. 6 is a fragmentary perspective view of a medical introducer of a medical device introduction system having an imaging device positioned in one of a plurality of access ports and having a pair of medical instruments or tools positioned in another one of a plurality of access ports according to the present invention;

FIG. 7 is an enlarged transverse sectional view of a medical introducer of a medical device introduction system taken along line 7—7 of FIG. 6 and which shows a pair of expandable lumen in the collapsed position, an expandable lumen in a first open position, and a pair of non-expandable lumen without instruments, tools, or other medical devices positioned therein according to the present invention;

FIG. 8 is an enlarged transverse sectional view of a medical introducer of a medical device introduction system taken along line 8—8 of FIG. 6 and which shows a collapsed lumen, a collapsed lumen which has been expanded by the inserting of a medical instrument, tool, or other medical device therein, an expandable lumen which has expanded from an open position to an enlarged position, and a pair of non-expandable lumen according to the present invention;

FIG. 9 is a fragmentary longitudinal sectional view of an expandable lumen of a medical introducer of a medical device introduction system taken along line 9—9 of FIG. 6 which shows an expandable lumen in both a collapsed position and an expanded position according to the present invention;

FIG. 10 is a fragmentary longitudinal sectional view of an expandable lumen having a plurality of medical instruments, tools, or other medical devices positioned therein of a medical introducer of a medical device introduction system taken along line 10—10 of FIG. 6 and which shows the expansion from an open position to an expanded position being further opened according to the present invention;

FIG. 12 is a fragmentary top plan view of a distal portion of a medical introducer of a medical device introduction system which shows the variety of lengths X of the distal end portion of the introducer in relation to a first inflatable portion of the introducer according to the present invention;

FIG. 13 is a fragmentary perspective view of a distal portion of a medical introducer of a medical device introduction system which shows the inflation of first and second inflatable portions of the introducer according to the present invention;

FIG. 14 is a top plan view of another embodiment of a medical introducer of a medical device introduction system which shows a pivotal proximal portion which provides various angular approaches during medical procedures according to the present invention;

FIGS. 17A–17B are perspective views of the insertion of a medical introducer of another embodiment of a medical device introduction system and which includes a cannula being used on a male patient according to the present invention; and FIG. 18 is a fragmentary schematic view of a medical device introduction system which shows a use of a picture within a picture when at least two imaging devices are inserted into a medical introducer, one directly through one of the plurality of access ports and another one through a steerable working channel device which is also inserted into another one of the plurality of access ports of the medical introducer according to the present invention.

DETAILED DESCRIPTION OF PREFERRED EMBODIMENTS

Figure 11:
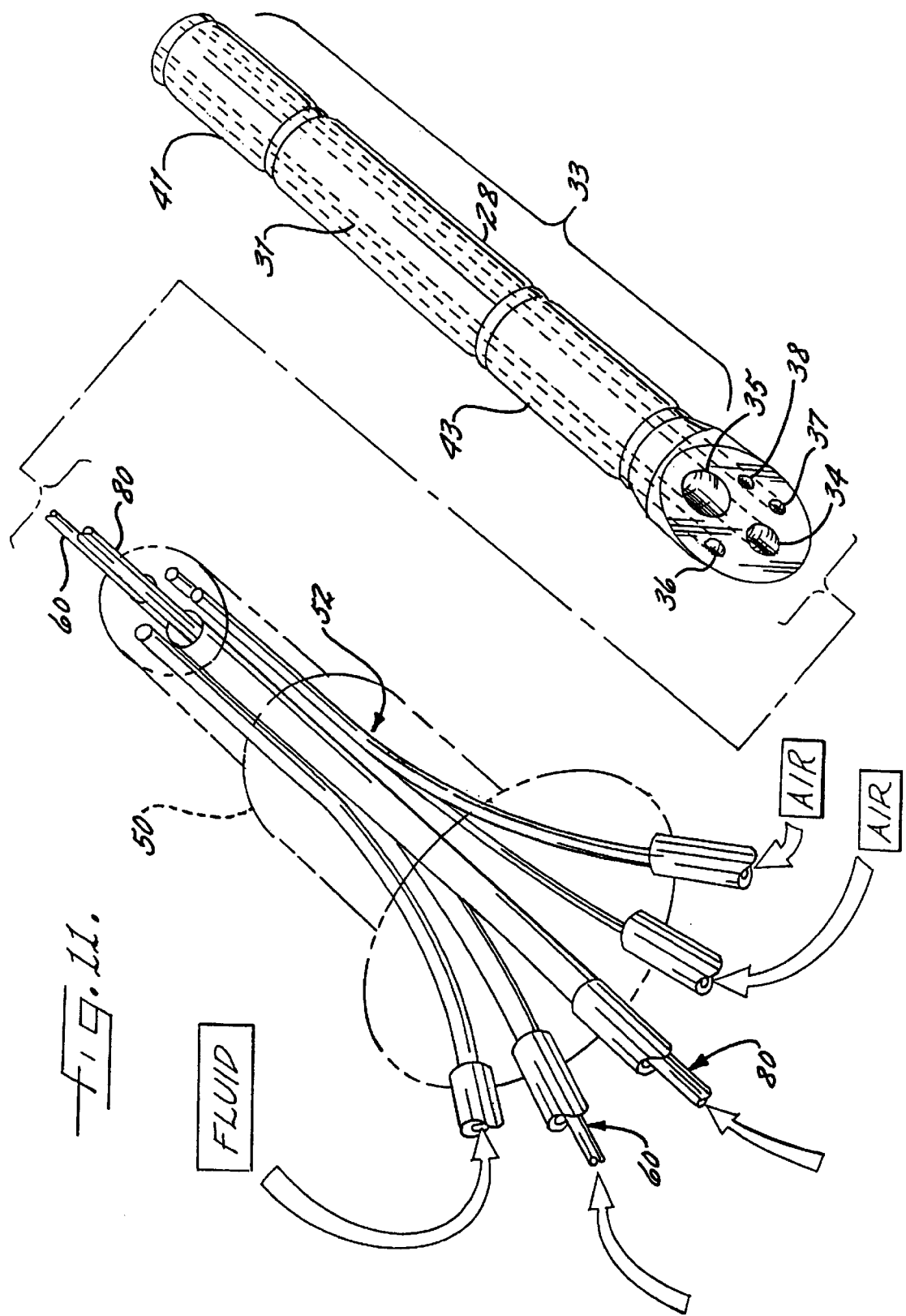
FIG. 11 is a schematic perspective view of proximal and distal portions of a medical introducer of a medical device introduction system which shows the manifold, plurality of access ports, a plurality of lumen, and the introduction of medical instruments, tools, other medical devices, air, and/or other fluid according to the present invention.

The present invention will now be described more fully hereinafter with reference to the accompanying drawings, in which preferred embodiments of the invention are shown. This invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime and/or double prime notation, if used, indicate similar elements in alternative embodiments.

FIGS. 1–4 and 15–18 illustrate a medical device introduction system 20 which includes a medical introducer 30, at least one imaging device 60, and a separate working channel device 80 which is preferably steerable. A medical introducer or medical sheath introducer 30, as understood in the medical arts, is an instrument that is used to introduce a tube, stents, catheters, and/or other medical devices into a portion of a patient's body, e.g., a body cavity, a body space or potential space, a vein, an artery, or a body vessel.

Advantageously, the separate steerable working channel device 80 and the imaging device 60 when inserted into one 34 of a plurality of lumen 34, 35, 36, 37, 38 of the medical introducer 30 are separately controllable by a user thereof independent of each other. As simplified, the separate working channel device 80 can also be a non-steerable working channel in the since that it does not have steering means associated therewith and the separate control would include the in and out motion of the device 80 within a lumen of the introducer 30. The steering capability, however, advantageously provides more control of the distal tip of the working channel which can also be used to place various fluids, i.e., liquid or gas, as well as medical devices or instruments at desired locations. The medical introducer 30 as well is preferably separately controllable independent of the imaging device 60 positioned therein and independent of the steerable working channel device 80. Such a system 20 can advantageously be used in many medical procedures including gynecological, fertility, hysteroscopy, or prostate type applications as illustrated in FIGS. 2, 15, and 17A–17B. For example, the medical device introduction system 20 and medical introducer 30 thereof advantageously has applications for procedures and products related to insemination and profusion, intrauterine blastocyst/embryo transfer, endoscopic evaluation and operations, laproscopy (i.e., culdoscopy, transvaginal hydro laparoscopy), and/or falloscopy. Accordingly, both fluid management and medical instruments usage can be a function of the working channel device 80 independent of or separate from both the imaging device 60 and the medical introducer 30.

The medical introducer 30 preferably has an introducer body 31 which includes a distal body portion 33, a proximal body portion 50, and a medial body portion 45 extending between the distal body portion 33 and the proximal body portion 50. A plurality of lumen 34, 35, 36, 37, 38 extend through the introducer body 31 as illustrated. The medical introducer 30 preferably has a length in the range of 3.5 to 10.5 inches, depending on the application, which makes it much larger than many simple single port introducers known in the art.

As perhaps best shown in FIGS. 2–3 and 6, the proximal portion 50 of the body 31 of the medical introducer 30 preferably is enlarged, e.g., bulbous, and a user interface 55 is preferably formed at a proximal end of the enlarged proximal body portion 50. The medical introducer 30 is preferably formed in a molding process, as understood by those skilled in the art, by a plastic or polymeric material. Different portions of the medical introducer 30, however, such as the enlarged proximal portion 50, can be formed so as to have different rigidities and/or hardness. For example, the enlarged proximal portion 50 is preferably semi-soft or flexible.

The user interface 55, for example, can include a plurality of separate proximal tubes 56 extending outwardly from the enlarged proximal body portion 50. Each of the plurality of separate proximal tubes 56 preferably includes a seal 58 associated therewith for allowing medical devices and/or fluid, e.g., gas or liquid, to pass therethrough toward a distal end of the introducer body 31 and for inhibiting fluid from passing therethrough toward the proximal end of the separate proximal tube 56. Such seals 58, e.g., duckbill or other one way valves, including luer fittings associated therewith, are well understood by those skilled in the art. The seals 58 also preferably provide frictional or abutting contact with the outer surface of the elongate tube portion of the working channel device 80 which can advantageously be used to retain the working channel device 80 in a selected position.

The medical devices, for example, can include various imaging devices such as fiberscopes, cameras or charge couple devices, or ultrasound devices, cutting tools, sampling tools, irrigation devices, various medical instruments, or tools for performing implants.

As illustrated, the introducer body 31 generally has a narrower distal end portion than a proximal end portion thereof. The narrower distal end portion, for example, preferably has an outside diameter within the range of about 1.5 to 10.5 millimeters depending on the application. For example, an insemination and profusion introducer preferably has an outside diameter range of the distal end portion from about 2.0 to 4.0 millimeters, a hysteroscopic introducer preferably has an outside diameter range of a distal end portion from about 2.0 to 5.0 millimeters, and a transvaginal hydro laparoscopy introducer preferably has an outside diameter range of a distal end portion from about 2.0 to 10.0 millimeters. An imaging device 60, such as a fiberscope, preferably has an outside diameter of about 1.0 to 3.0 millimeters, and a working channel device preferably has an outside diameter range of about 1.0 to 3.5 millimeters.

The enlarged proximal body portion 50 preferably also includes a manifold 52 connecting the plurality of separate proximal tubes 56 to the plurality of lumen of the introducer body 31 (see FIGS. 6 and 11). At least one of the plurality of lumen 34, 35, 36, 37, 38 of the introducer body 31 advantageously transitions from a smaller inside diameter, e.g., about 0.5 millimeters, in a distal end portion of the introducer body 31 to a larger inside diameter, e.g., about 1.5 millimeters, in a medial portion 45 of the introducer body 31 to thereby allow tissue such as removed during surgical procedures to more readily pass therethrough. The smaller lumen as illustrated preferably has an inside diameter which ranges from 0.5 to 2.0 millimeters, and the larger lumen as illustrated has an inside diameter of 1.0–3.0 millimeters. Although this range can mean that the lumen has a uniform diameter throughout which falls within the range, preferably as described above this range represents a transition from smaller to larger diameter within this range.

Also, as illustrated in the alternative embodiments of FIGS. 6–10, at least one, e.g., two lumen 37', 38', of the plurality of lumen 34', 35', 36', 37', 38' of the medical introducer 30' can advantageously be biased to a collapsed or fully closed position and elastically stretches to an open position to receive a medical device or fluid when positioned therein. In addition, or alternatively, at least one 36' of the plurality of lumen 34', 35', 36', 37', 38' of the medical introducer 30' can be biased in an open position and elastically stretch to an enlarged position for receiving a plurality of medical devices, an enlarged medical device, or additional fluid capacity therethrough.

As best shown in FIGS. 2–4 and 11–13, the distal portion 33 of the introducer body 31 preferably includes at least one inflatable portion 41 associated with the outer surface 28 of a predetermined distal end portion thereof for inflating the outer surface of the predetermined distal end portion from a collapsed to an enlarged position to thereby distend or enlarge a cavity, space, or portion of a patient's body and/or block fluid passage from the body cavity when the medical introducer is positioned therein. This inflatable portion 41, more preferably, is a first inflatable portion. The introducer body 31 also preferably includes a second inflatable portion 43 associated with the outer surface of a predetermined proximal end portion for inflating the outer surface of the predetermined proximal end portion from a collapsed to an enlarged position to thereby provide a stop or stop guide for stopping the further insertion of the medical introducer 30 within a body cavity (see, e.g., FIGS. 2 and 15). Either the first or second inflatable portions 41, 43 also advantageously can be located or positioned at various distances X (see, e.g., FIG. 12) from the distal tip of the introducer 30 according to the present invention so that the introducer 30 is customized or tailored for specific applications or procedures. These features, for example, provides flexibility, enhance positioning of the introducer 30, enhance visibility, and enhance performance of various medical procedures.

In another alternate embodiment, as best shown in FIG. 14, the medial portion 45" of the introducer body 31" of a medical introducer 30" according to the present invention can include body pivoting means 47 for separately pivoting either the distal end portion 33" and/or medial portion 45" or the proximal end portion 50" so that the plane of the longitudinal extent of the distal end portion 33" extends transverse to the plane of the longitudinal extent of the proximal end portion 50". The body pivoting means 47, for example, is preferably a flexible and pivotal portion of the medial portion of the tube and has a plurality of reinforcing ribs 48. The flexing is preferably in a semi-rigid manner so that the proximal end portion 50" stays in a user selected location until adjusted or pivoted to another position. Such structures are well understood by those in the plastic tubing art. FIGS. 17A–17B illustrate an additional feature of the medical device introduction system 20 of the present invention which includes the use of one or more endoscopic devices, e.g., preferably provided by a trocar system, namely a cannula 100, a valve 105 positioned on a proximal end of the cannula, and a trocar 110 positioned to be inserted through the valve 105 and the cannula 100, through which the medical introducer 30 can be inserted. Such a trocar system, for example, can be used for prostate surgery, e.g., on a male patient as illustrated. In these applications, a portion of the patients body needs to be penetrated or opened where a body cavity does not provide a ready opening. As understood by those skilled in the art, a trocar system or other endoscopic device(s) assists in providing a path through which the medical introducer 30 can enter the portion of the patient's body into which a medical procedure is desired to be performed. The medical device introduction system 20 then provides the advantageous, benefits, and capabilities as described above and further herein.

Figure 15:
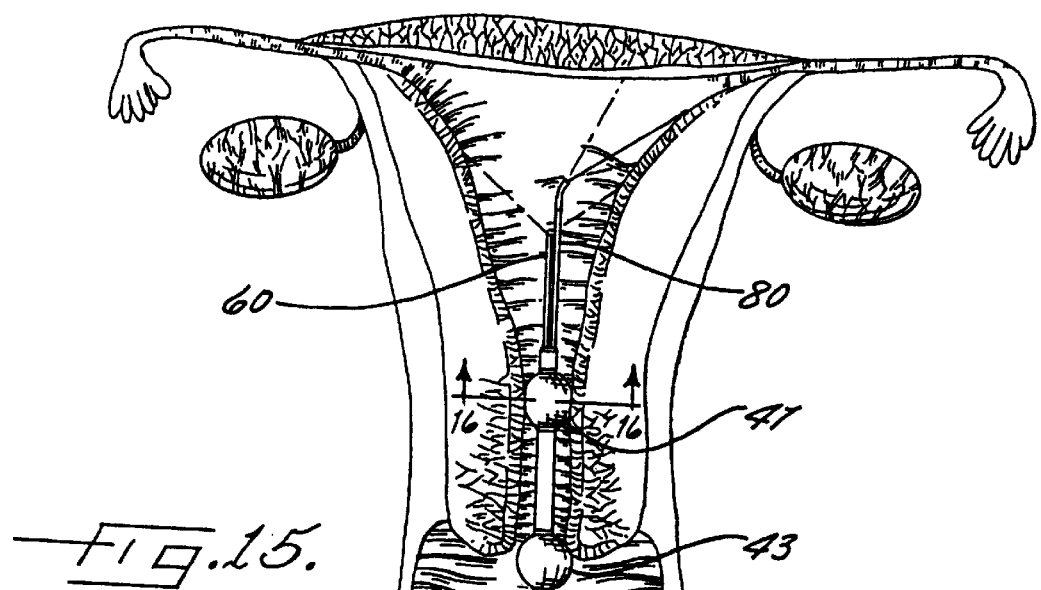
FIG. 15 is an environmental perspective view of a medical device introduction system being used on a female patient and which includes an imaging device inserted into one of a plurality of access ports of a medical introducer and a steerable working channel in the form of a multiple lumen working channel device inserted into another one of the plurality of access ports of the medical introducer to show the separate and independent operation of the imaging device and the steerable working channel according to the present invention.
Figure 16:
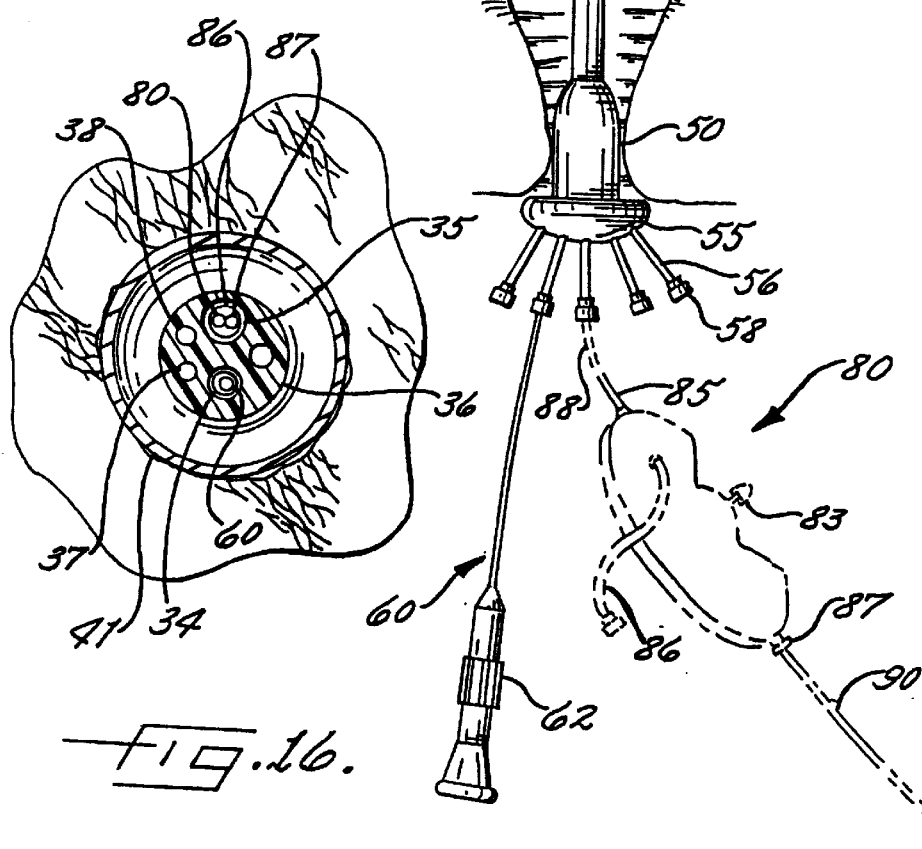
FIG. 16 is an enlarged transverse sectional view of a medical introducer of a medical device introduction system taken along line 16—16 of FIG. 15 and which shows the plurality of working channels of the separate multiple lumen working channel device when inserted into the medical introducer according to the present invention.

The medical introducer 30 of the present invention further preferably includes imaging device position maintaining means 32 associated therewith for maintaining the imaging device 60, e.g., preferably a distal end portion thereof, in at least one of a plurality of possible positions, e.g., rotational and linear, manually selected by a user thereof (see FIGS. 4 and 15). The imaging device 60, as understood by those skilled in the art, can move in and out and be held or maintained in a selected position as well as radially or rotationally such as for off-set scopes, e.g., 15 or 30 degrees, etc. The position maintaining means 32 preferably has at least portions of an inner surface of the one predetermined lumen 34 having slippage inhibiting means 39 associated therewith so that at least portions of an outer surface of an imaging device 60 do not readily slip when engaged therewith. Without the slippage inhibiting means 39 the imaging device 60 would otherwise be allowed to readily slippingly rotate to different positions within the lumen in which it is positioned. The slippage inhibiting means 39 preferably includes at least portions of the inner surface of the one predetermined lumen abuttingly contacting, e.g., frictional contact, at least portions of an outer surface of an imaging device 60 so that the abuttingly contacting relationship between the portions of the inner and outer surfaces maintain the imaging device 60 in a selected position. For example, the slippage inhibiting means 39 preferably can further be provided by portions of the inner surface of the one predetermined lumen having a first predetermined inside diameter portion, a second predetermined inside diameter portion coextensive with and having a smaller inside diameter than the first predetermined inside diameter portion, and a third predetermined inside diameter portion coextensive with and having a larger inside diameter than the second predetermined inside diameter portion (see FIG. 4). Other slippage inhibiting means 39 such as roughened surfaces with a plurality of raised bumps, gripping structures, or positional locks, as understood by those skilled in the art, can be used as well.

As described above, the medical device introduction system 20 also includes at least one imaging device 60 positioned in a predetermined one of the plurality of lumen 34, 35, 36, 37, 38 of the medical introducer 30 so that the imaging device 60 is separately controllable independent of the medical introducer 30. The imaging device 60 advantageously can include at least one of the following: an optical scope, e.g., a fiberscope, an ultrasound or other sonic instrument, or a camera positioned on a distal end portion of an elongate shaft, e.g., a "chip-on-a-stick", as understood by those skilled in the art. These imaging devices 60 are preferably connected to a monitor or other display 65 for viewing a picture of within the portion of the patient's body. The imaging device 60 can also include an ocular 62 or other portions to adjust focus or light intensity.

As perhaps best illustrated in FIG. 15, the medical device introduction system 20 also preferably includes a separate steerable working channel device 80, such as a multiple lumen working channel device, positioned in at least one other of the plurality of lumen of the medical introducer 30 so that the separate steerable working channel device 80 and the imaging device 60 are separately controllable by a user thereof independent of each other. The separate steerable working channel device 80 preferably includes an elongate tube 85 portion having at least one lumen 86 formed therein which defines the working channel and steering means 88 associated with the elongate tube portion 85 for steering the elongate tube portion 85. The steerable working channel device 80 preferably controls the steering of the working channel by the use of controlling means, e.g., preferably provided by a control knob or deflector lever 83, connected to the steering means 88 and to a catheter body 81 as illustrated. The steering means 88, for example, can be provided by control wires (shown by phantom lines) longitudinally connecting the distal end of the elongate tube portion 85 with the control knob 83 as understood by those skilled in the art. Also, various other steering means 88 as understood by those skilled in the art, such as one or more position deflectors associated with the elongate tube portion 85, can be used as well according to the present invention.

This lumen 86 of the steerable working channel device 80 is preferably a first lumen of a plurality of lumen 86, 87. The imaging device 60 which is inserted into the medical introducer 30 as described above can be a first imaging device, and the system 20 can further include a second imaging device 90 positioned in another one 87 of the plurality of lumen 86, 87 of the steerable working channel device 80 (see FIG. 18). The second imaging device 90, like the first imaging device 60, can vary depending on the medical procedure desired to be performed. The second imaging device 90 can also include at least one of the following: an optical scope, e.g., a fiberscope, an ultrasound instrument, or a camera positioned on a distal end portion of an elongate shaft, e.g., a "chip-on-a-stick", as understood by those skilled in the art. The second imaging device advantageously allows a picture-within-a-picture as shown in FIG. 18 to be used to further enhance visibility and to provide additional knowledge about the portion with the patient's body being examined, biopsied, implanted, operated upon or other medical procedure performed.

As illustrated in FIGS. 1–18, and as described above, the present invention also provides methods of performing a medical procedure. A method preferably includes inserting an imaging device 60 through a medical introducer 30 positioned within a portion of a patient's body, positioning the imaging device 60 to produce an image from within the portion of the patient's body, inserting a steerable working channel device 80 through the same medical introducer 30, and controlling the steering of the steerable working channel device 80 separately and independently from the positioning of the imaging device 60. The positioning step, for example, can advantageously include rotating the imaging device 60 to a selected position and maintaining the selected position of the imaging device 60 without the necessity of a user thereof manually maintaining the position.

Also, the imaging device 60 is preferably a first imaging device, the steerable working channel device 80 can also include an imaging channel 87, and the method further can include inserting a second imaging device 90 through the imaging channel 87 of the steerable working channel device 80 when positioned within the medical introducer 30 to also produce an image from within the portion of the patient's body. The medical introducer 30 also can include at least a first inflatable portion 41 associated with the distal end portion 33 of the medical introducer 30, and the method can include inflating the first inflatable portion 41 when the medical introducer 30 is positioned within the portion of the patient's body. The medical introducer 30 can further include a second inflatable portion 43 associated with the distal end portion 33 of the medical introducer 30, and the method can include inflating the second inflatable portion 43 when the medical introducer 30 is positioned within a patient's body.

The method can still further include one or more of the steps of supplying fluid to the portion of the body through yet another lumen of the plurality of lumen 34, 35, 36, 37, 38 of the same medical introducer 30, visually viewing the produced image from within the portion of the patient's body, and conducting a surgical procedure through the steerable working channel device 80 when the steerable working channel device 80 is inserted within the portion of the patient's body. Also, to assist with fertility problems for example, the method can include inserting at least one of the following through the steerable working channel device 80 when inserted within the portion of the body: at least one gamete, at least one sperm, at least one egg or og, at least one embryo, or at least one blastocyst.

Another method preferably includes positioning an imaging device 60 through a first lumen of a medical introducer 30 positioned within a uterine cavity of a body of a patient to thereby produce an image from within the uterine cavity, inserting a steerable working channel device 80 through a second lumen of the same medical introducer 30, and inserting at least one of the following through the steerable working channel device 80 when inserted within the uterine cavity: at least one gamete, at least one sperm, at least one egg or og, at least one embryo, or at least one blastocyst. The positioning step, for example, can advantageously include rotating the imaging device 60 to a selected position and maintaining the position of the imaging device 60 in the selected position without the necessity of a user thereof manually maintaining the position.

Also, like the other method described above, the imaging device 60 is preferably a first imaging device 60, and the steerable working channel device 80, in addition to the working channel 86, can also include an imaging channel 87. The method further can include inserting a second imaging device 90 through the imaging channel 87 of the steerable working channel device 80 when positioned within the medical introducer 30 to also produce an image from within the portion of the patient's body.

Additionally, the medical introducer 30 can include at least a first inflatable portion 41 associated with the distal end portion 33 of the medical introducer 30, and the method can include inflating the first inflatable portion 41 when the medical introducer 30 is positioned within the portion of the patient's body. The medical introducer 30 can also include a second inflatable portion 43 associated with the distal end portion 33 of the medical introducer 3b, and the method can include inflating the second inflatable portion 43 when the medical introducer 30 is positioned within a patient's body. The method can still further include one or more of the steps of supplying fluid to the portion of the patient's body through yet another lumen of the plurality of lumen 34, 35, 36, 37, 38 of the same medical introducer 30 and visually viewing the produced image from within the portion of the patient's body.

Yet another method of performing a medical procedure preferably includes inserting an endoscopic device, such as preferably provided by a cannula 100, into a portion of a patient's body, inserting a medical introducer 30 having a plurality of lumen 34, 35, 36, 37, 38 extending therethrough into the endoscopic device, inserting a steerable working channel device 80 through one of the plurality of lumen 34, 35, 36, 37, 38 of the same medical introducer 30, and controlling the steering of the steerable working channel device 30. The endoscopic device is preferably provided by a cannula 100, e.g., see FIGS. 17A–17B, as understood by those skilled in the art. The method can also include inserting an imaging device 60 through another one of the plurality of lumen 34, 35, 36, 37, 38 of the same medical introducer 30 positioned within the cannula 100 and positioning the imaging device 60 to produce an image from within the portion of the patient's body. The positioning step, for example, can advantageously include rotating the imaging device 60 to a selected position and maintaining the position of the imaging device 60 in the selected position without the necessity of a user thereof manually maintaining the position.

Likewise, the imaging device 60 is preferably a first imaging device, the steerable working channel device 80 can include an imaging channel 87, and the method further can include inserting a second imaging device 90 through the imaging channel 87 of the steerable working channel device 80 when positioned within the medical introducer 30 to also produce an image from within the portion of the patient's body.

Additionally, the medical introducer 30 can also include at least a first inflatable portion 41 associated with the distal end portion 33 of the medical introducer 30, and the method can include inflating the first inflatable portion 41 when the medical introducer 30 is positioned within the portion of the patient's body. The medical introducer 30 can also include a second inflatable portion 43 associated with the distal end portion 33 of the medical introducer 30, and the method can include inflating the second inflatable portion 43 when the medical introducer 30 is positioned within a patient's body. The method can still further include one or more of the steps of supplying fluid to the portion of the body through yet another lumen of the plurality of lumen of the same medical introducer 30, visually viewing the produced image from within the portion of the patient's body, and conducting a surgical procedure through the steerable working channel device 80 when the steerable working channel device 80 is inserted within the portion of the patient's body. Also, for example, the method can include inserting at least one of the following through the steerable working channel device 80 when inserted within the portion of the body: at least one gamete, at least one sperm, at least one egg or og, at least one embryo, or at least one blastocyst.

The present invention also includes a method of viewing within a portion of a patient's body. The method preferably includes inserting an imaging device 60 through one of a plurality of lumen 34, 35, 36, 37, 38 of a medical introducer 30 positioned within a portion of a patient's body, moving the imaging device 60 to a selected position, maintaining the position of the imaging device 60 in the selected position by use of the medical introducer 30 and without the necessity of a user thereof manually maintaining the position, producing an image from within the portion of the patient's body, inserting a steerable working channel device 80 through another one of the plurality of lumen 34, 35, 36, 37, 38 of the same medical introducer 30, and controlling the steering of the steerable working channel device 80 without moving the position of the imaging device 60. The imaging device 60 can be a first imaging device, the steerable working channel device 80 can include an imaging channel 87, and the method can further include inserting a second imaging device 90 through the imaging channel 87 of the steerable working channel device 80 when positioned within the medical introducer 30 to also produce an image from within the portion of the patient's body.

Also, the method can include the medical introducer 30 having at least a first inflatable portion 41 associated with the distal end portion 33 of the medical introducer 30, and inflating the first inflatable portion 41 when the medical introducer 30 is positioned within the portion of the patient's body. Additionally, the medical introducer 30 can include a second inflatable portion 43 associated with the distal end portion of the medical introducer 30, and the method further include inflating the second inflatable portion 43 when the medical introducer 30 is positioned within a patient's body.

Further, the method can include one or more of the steps of supplying fluid to the portion of the body through yet another lumen of the plurality of lumen 34, 35, 36, 37, 38 of the same medical introducer 30, visually viewing the produced image from within the portion of the patient's body, and conducting a surgical procedure through the steerable working channel device 80 when the steerable working channel device 80 is inserted within the portion of the patient's body.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A medical device introduction system comprising:
   a medical introducer having an introducer body, a plurality of lumen formed therein, and imaging device position maintaining means for maintaining a rotational position of a distal end portion of an imaging device when positioned within a predetermined one of the plurality of lumen;

an imaging device positioned in the predetermined one of the plurality of lumen of said medical introducer and moveable with respect to inner surfaces of the predetermined one of the plurality of lumen, the imaging device contacting said imaging device position maintaining means to thereby maintain the imaging device in a rotational position manually selected by a user thereof; and a separate steerable working channel device positioned in at least one other of the plurality of lumen of the medical introducer so that the separate steerable working channel device and the imaging device are separately controllable by a user thereof independent of each other, said separate steerable working channel device including an elongate tube portion having at least one lumen formed therein which defines a working channel, steering means associated with the elongate tube portion for steering the elongate tube portion, and controlling means connected to said steering means for controlling the steering of the working channel.

2. A system as defined in claim 1, wherein at least one of the plurality of lumen of said medical introducer is biased to a collapse position and elastically stretches to an open position to receive a medical device positioned therein, or to accommodate the flow of a fluid therethrough.

3. A system as defined in claim 1, wherein at least one of the plurality of lumen of said medical introducer is biased in an open position and substanitially elastically stretches to an enlarged position for receiving a plurality of medical devices, an enlarged medical device, or additional fluid capacity therethrough.

4. A system as defined in claim 1, wherein at least one of said plurality of lumen of said medical introducer transitions from a smaller inside diameter in a distal end portion of said introducer body to a larger inside diameter in a medial portion of said introducer body to thereby allow tissue such as removed during surgical procedures to more readily pass therethrough.

5. A system as defined in claim 1, wherein said body of said medical introducer includes an enlarged proximal body portion and a user interface formed at a proximal end of the enlarged proximal body portion, said user interface including a plurality of separate proximal tubes extending outwardly from the enlarged proximal body portion, each of the plurality of separate proximal tubes including a seal associated therewith for allowing medical devices or fluid to pass therethrough toward a distal end of said introducer body and for inhibiting fluid from passing therethrough toward the proximal end of the proximal tube.

6. A system as defined in claim 5, wherein the introducer body has a narrower distal end portion than a proximal end portion thereof, and wherein said enlarged proximal body portion includes a manifold connecting the plurality of separate proximal tubes to the plurality of lumen of said introducer body.

7. A system as defined in claim 1, wherein said body of said medical introducer includes a distal end portion, a proximal end portion, and a medial portion extending between the distal end portion and the proximal end portion, said medial portion including body pivoting means for separately pivoting either said distal end portion or said proximal end portion so that the plane of the longitudinal extent of the distal end portion extends transverse to the plane of the longitudinal extent of the proximal end portion.

8. A system as defined in claim 1, wherein said introducer body includes at least one inflatable portion associated with the outer surface of a predetermined distal end portion thereof for inflating the outer surface of the predetermined distal end portion from a collapsed to an enlarged position to thereby block fluid passage from a body cavity when said medical introducer is positioned therein.

9. A system as defined in claim 8, wherein said introducer body includes a first and a second inflatable portion associated with the outer surface of a predetermined proximal end portion for inflating the outer surface of the predetermined proximal end portion from a collapsed to an enlarged position to thereby provide a stop for stopping the further insertion of said medical introducer within a body cavity.

10. A system as defined in claim 9, wherein said imaging device includes at least one of the following: an optical scope, an ultrasound instrument, or a camera positioned on a distal end portion of an elongate shaft.

11. A system as defined in claim 10, wherein said at least one lumen of said steerable working channel device further comprises a first and second lumen of a plurality of lumen, wherein the first lumen of said elongate tube portion of said separate steerable working channel device houses a first imaging device, and wherein the second lumen of said elongate tube portion of said separate steerable working channel device houses a second imaging device.

12. A system as defined in claim 11, wherein said second imaging device includes at least one of the following: an optical scope, an ultrasound instrument, or a camera positioned on a distal end portion of an elongate shaft.

13. A system as defined in claim 1, wherein said imaging device position maintaining means comprises at least portions of an inner surface of the one predetermined lumen having slippage inhibiting means associated therewith so that at least portions of an outer surface of said imaging device do not readily slip when engaged therewith to otherwise thereby allow said imaging device to readily slippingly rotate to different positions.

14. A system as defined in claim 13, wherein said slippage inhibiting means includes at least portions of the inner surface of the one predetermined lumen abuttingly contacting at least portions of an outer surface of said imaging device so that the abuttingly contacting relationship between the portions of the inner and outer surfaces maintain the imaging device in a selected position.

15. A system as defined in claim 14, wherein the slippage inhibiting means further includes portions of the inner surface of the one predetermined lumen having a first predetermined inside diameter portion, a second predetermined inside diameter portion coextensive with and having a smaller inside diameter than the first predetermined inside diameter portion, and a third predetermined inside diameter portion coextensive with and having a larger inside diameter than the second predetermined inside diameter portion.

16. A system as defined in claim 1, further comprising an endoscopic device for positioning within a portion of a patient's body, said endoscopic device including at least a cannula.

17. A system as defined in claim 1, wherein the imaging device is further positioned to slidably engage one of the plurality of lumen of the medical introducer so that the imaging device slides along interior portions of the predetermined one of the plurality of lumen of the medical introducer.

18. A medical device introduction system comprising:
a medical introducer having an introducer body and a plurality of lumen formed therein;

an imaging device positioned in a predetermined one of the plurality of lumen of said medical introducer so that the imaging device is separately movable independent of said medical introducer; and a separate steerable working channel device positioned in at least one other of the plurality of lumen of said medical introducer so that the separate working channel device and the imaging device are separately controlled by a user thereof independent of each other, said separate working channel device including an elongate tube portion having at least one lumen formed therein which defines the working channel.

19. A system as defined in claim 18, wherein at least one of the plurality of lumen of said medical introducer is biased to a collapse position and elastically stretches to an open position to receive medical device positioned therein, or to accommodate the flow of a fluid therethrough.

20. A system as defined in claim 18, wherein at least one of the plurality of lumen of said medical introducer is biased in an open position and substantially elastically stretches to an enlarged position for receiving a plurality of medical devices, an enlarged medical device, or additional fluid capacity therethrough.

21. A system as defined in claim 18, wherein at least one of said plurality of lumen of said medical introducer transitions from a smaller inside diameter in a distal end portion of said introducer body to a larger inside diameter in a medial portion of said introducer body to thereby allow tissue such as removed during surgical procedures to more readily pass therethrough.

22. A system as defined in claim 18, wherein said body of said medical introducer includes an enlarged proximal body portion and a user interface formed at a proximal end of the enlarged proximal body portion, said user interface including a plurality of separate proximal tubes extending outwardly from the enlarged proximal body portion, each of the plurality of separate proximal tubes including a seal associated therewith for allowing medical devices or fluid to pass therethrough toward a distal end of said introducer body and for inhibiting fluid from passing therethrough toward the proximal end of the proximal tube.

23. A system as defined in claim 22, wherein the introducer body has a narrower distal end portion than a proximal end portion thereof, and wherein said enlarged proximal body portion includes a manifold connecting the plurality of separate proximal tubes to the plurality of lumen of said introducer body.

24. A system as defined in claim 18, wherein said body of said medical introducer includes a distal end portion, a proximal end portion, and a medial portion extending between the distal end portion and the proximal end portion, said medial portion including body pivoting means for separately pivoting either said distal end portion or said proximal end portion so that the plane of the longitudinal extent of the distal end portion extends transverse to the plane of the longitudinal extent of the proximal end portion.

25. A system as defined in claim 18, wherein said introducer body includes at least one inflatable portion associated with the outer surface of a predetermined distal end portion thereof for inflating the outer surface of the predetermined distal end portion from a collapsed to an enlarged position to thereby block fluid passage from a body cavity when said medical introducer is positioned therein.

26. A system as defined in claim 25, wherein said introducer body includes a first and a second inflatable portion associated with the outer surface of a predetermined proximal end portion for inflating the outer surface of the predetermined proximal end portion from a collapsed to an enlarged position to thereby provide a stop for stopping the further insertion of said medical introducer within a body cavity.

27. A system as defined in claim 19, wherein said imaging device includes at least one of the following:

an optical scope, an ultrasound instrument, or a camera positioned on a distal end portion of an elongate shaft.

28. A system as defined in claim 18, wherein said separate working channel device further includes steering means associated with the elongate tube portion for steering the elongate tube portion so as to define a steerable working channel device, and wherein said at least one lumen of said steerable working channel device comprises a first lumen of a plurality of lumen.

29. A system as defined in claim 28, further comprising a second imaging device positioned in a second of the plurality of lumen of said steerable working channel device, and wherein said second imaging device includes at least one of the following: an optical scope, an ultrasound instrument, or a camera positioned on a distal end portion of an elongate shaft.

30. A system as defined in claim 18, wherein said medical introducer further includes imaging device position maintaining means associated therewith for maintaining the imaging device in at least one of a plurality of possible rotational positions selected by a user thereof.

31. A system as defined in claim 30, wherein said imaging device position maintaining means comprises at least portions of an inner surface of the one predetermined lumen having slippage inhibiting means associated therewith so that at least portions of an outer surface of said imaging device do not readily slip when engaged therewith to otherwise thereby allow said imaging device to readily slippingly rotate to different positions.

32. A system as defined in claim 31, wherein said slippage inhibiting means includes at least portions of the inner surface of the one predetermined lumen abuttingly contacting at least portions of an outer surface of said imaging device so that the abuttingly contacting relationship between the portions of the inner and outer surfaces maintain the imaging device in a selected position.

33. A system as defined in claim 32, wherein the slippage inhibiting means further includes portions of the inner surface of the one predetermined lumen having a first predetermined inside diameter portion, a second predetermined inside diameter portion coextensive with and having a smaller inside diameter than the first predetermined inside diameter portion, and a third predetermined inside diameter portion coextensive with and having a larger inside diameter than the second predetermined inside diameter portion.

34. A system as defined in claim 18, further comprising an endoscopic device for positioning within a portion of a patient's body.

35. A system as defined in claim 18, wherein the imaging device is further positioned to slidably engage one of the plurality of lumen of the medical introducer so that the imaging device slides along interior portions of the predetermined one of the plurality of lumen of the medical introducer.

36. A medical introducer for introducing medical devices therethrough, the medical introducer comprising:

an introducer body;

a plurality of lumen formed in said introducer body; and imaging device position maintaining means associated with at least an inner surface of a predetermined one of the plurality of lumen for maintaining a rotational position of a distal end portion of an imaging device when positioned within the predetermined one of the plurality of lumen.

37. A medical introducer as defined in claim 36, wherein at least one of the plurality of lumen is biased to a collapse position and elastically stretches to an open position to receive a medical device positioned therein, or to accommodate the flow of a fluid therethrough.

38. A medical introducer as defined in claim 36, wherein at least one of the plurality of lumen is biased in an open position and substantially elastically stretches to an enlarged position for receiving a plurality of medical devices, an enlarged medical device, or additional fluid capacity therethrough.

39. A medical introducer as defined in claim 36, wherein at least one of said plurality of lumen transitions from a smaller inside diameter in a distal end portion of said introducer body to a larger inside diameter in a medial portion of said introducer body to thereby allow tissue such as removed during surgical procedures to more readily pass therethrough.

40. A medical introducer as defined in claim 36, wherein said body of said medical introducer includes an enlarged proximal body portion and a user interface formed at a proximal end of the enlarged proximal body portion, said user interface including a plurality of separate proximal tubes extending outwardly from the enlarged proximal body portion, each of the plurality of separate proximal tubes including a seal associated therewith for allowing medical devices or fluid to pass therethrough toward a distal end of said introducer body and for inhibiting fluid from passing therethrough toward the proximal end of the proximal tube.

41. A medical introducer as defined in claim 40, wherein the introducer body has a narrower distal end portion than a proximal end portion thereof, and wherein said enlarged proximal body portion includes a manifold connecting the plurality of separate proximal tubes to the plurality of lumen of said introducer body.

42. A medical introducer as defined in claim 36, wherein said body of said medical introducer includes a distal end portion, a proximal end portion, and a medial portion extending between the distal end portion and the proximal end portion, said medial portion including body pivoting means for separately pivoting either said distal end portion or said proximal end portion so that the plane of the longitudinal extent of the distal end portion extends transverse to the plane of the longitudinal extent of the proximal end portion.

43. A medical introducer as defined in claim 36, wherein said introducer body includes at least one inflatable portion associated with the outer surface of a predetermined distal end portion thereof for inflating the outer surface of the predetermined distal end portion from a collapsed to an enlarged position to thereby block fluid passage from a body cavity when said medical introducer is positioned therein.

44. A medical introducer as defined in claim 43, wherein said introducer body includes a first and a second inflatable portion associated with the outer surface of a predetermined proximal end portion for inflating the outer surface of the predetermined proximal end portion from a collapsed to an enlarged position to thereby provide a stop for stopping the further insertion of said medical introducer within a body cavity.

45. A medical introducer as defined in claim 36, wherein said imaging device position maintaining means comprises at least portions of an inner surface of the one predetermined lumen having slippage inhibiting means associated therewith so that at least portions of an outer surface of the imaging device do not readily slip when engaged therewith to otherwise thereby allow the imaging device to readily slippingly rotate to different positions.

46. A medical introducer as defined in claim 45, wherein said slippage inhibiting means includes at least portions of the inner surface of the one predetermined lumen abuttingly contacting at least portions of an outer surface of said imaging device so that the abuttingly contacting relationship between the portions of the inner and outer surfaces maintain the imaging device in a selected position.

47. A medical introducer as defined in claim 46, wherein the slippage inhibiting means further includes portions of the inner surface of the one predetermined lumen having a first predetermined inside diameter portion, a second predetermined inside diameter portion coextensive with and having a smaller inside diameter than the first predetermined inside diameter portion, and a third predetermined inside diameter portion coextensive with and having a larger inside diameter than the second predetermined inside diameter portion.

48. A medical introducer for introducing medical devices therethrough, the medical introducer comprising:
an introducer body including at least one inflatable portion associated with the outer surface of a predetermined distal end portion thereof for inflating the outer surface of the predetermined distal end portion from a collapsed to an enlarged position; and
a plurality of lumen formed therein, at least one of said plurality of lumen transitioning from a smaller inside diameter in a distal end portion of said introducer body to a larger inside diameter in a medial portion of said introducer body to thereby allow tissue such as removed during surgical procedures to more readily pass therethrough;
wherein said body of said medical introducer includes an enlarged proximal body portion an a user interface formed at a proximal end of the enlarged proximal body portion, said user interface including a plurality of separate proximal tubes extending outwardly from the enlarged proximal body portion, each of the plurality of separate proximal tubes including a seal associated therewith for allowing medical devices or fluid to pass therethrough toward a distal end of said introducer body and for inhibiting fluid from passing therethrough toward the proximal end of the proximal tube.

49. A medical introducer as defined in claim 48, wherein at least one of the plurality of lumen is biased to a collapse position and elastically stretches to an open position to receive a medical device positioned therein, or to accommodate the flow of a fluid therethrough.

50. A medical introducer as defined in claim 48, wherein at least one of the plurality of lumen is biased in an open position and elastically stretches to an enlarged position for receiving a plurality of medical devices, an enlarged medical device, or additional fluid capacity therethrough.

51. A medical introducer as defined in claim 48, wherein the introducer body has a narrower distal end portion than a proximal end portion thereof, and wherein said enlarged proximal body portion includes a manifold connecting the plurality of separate proximal tubes to the plurality of lumen of said introducer body.

52. A medical introducer as defined in claim 48, wherein said body of said medical introducer includes a distal end portion, a proximal end portion, and a medial portion extending between the distal end portion and the proximal end portion, said medial portion including body pivoting means for separately pivoting either said distal end portion or said proximal end portion so that the plane of the longitudinal extent of the distal end portion extends transverse to the plane of the longitudinal extent of the proximal end portion.

53. A medical introducer as defined in claim 48, wherein said introducer body includes a first and a second inflatable portion associated with the outer surface of a predetermined proximal end portion for inflating the outer surface of the predetermined proximal end portion from a collapsed to an enlarged position to thereby provide a stop for stopping the further insertion of the medical introducer within a body cavity.

54. A medical introducer as defined in claim 53, further comprising an imaging device, wherein the imaging device includes at least one of the following: an optical scope, an ultrasound instrument, or a camera positioned on a distal end portion of an elongate shaft.

55. A medical introducer as defined in claim 48, further comprising an imaging device position maintaining means which comprises at least portions of an inner surface of the one predetermined lumen having slippage inhibiting means associated therewith so that at least portions of an outer surface of the imaging device do not readily slip when engaged therewith to otherwise thereby allow the imaging device to readily slippingly rotate to different positions.

56. A medical introducer as defined in claim 55, wherein said slippage inhibiting means includes at least portions of the inner surface of the one predetermined lumen abuttingly contacting at least portions of an outer surface of said imaging device so that the abuttingly contacting relationship between the portions of the inner and outer surfaces maintain the imaging device in a selected position.

57. A medical introducer as defined in claim 56, wherein the slippage inhibiting means further includes portions of the inner surface of the one predetermined lumen having a first predetermined inside diameter portion, a second predetermined inside diameter portion coextensive with and having a smaller inside diameter than the first predetermined inside diameter portion, and a third predetermined inside diameter portion coextensive with and having a larger inside diameter than the second predetermined inside diameter portion.

58. A method of performing a medical procedure comprising the steps of:
  inserting an imaging device through a medical introducer having a proximal and distal end portion positioned within a portion of a patient's body;
  positioning the imaging device to produce an image from within the portion of the patient's body;
  inserting a steerable working channel device through the same medical introducer; and
  controlling the steering of the steerable working channel separately and independently from the positioning of the imaging device.

59. A method as defined in claim 58, wherein the steerable working channel device includes an imaging channel, and the method further comprising inserting a second imaging device through the imaging channel of the steerable working channel device when positioned within the medical introducer to also produce an image from within the portion of the patient's body.

60. A method as defined in claim 58, wherein the medical introducer includes at least a first inflatable portion associated with the distal end portion of the medical introducer, and the method further comprising inflating the first inflatable portion when the medical introducer is positioned within the portion of the patient's body.

61. A method as defined in claim 60, wherein the medical introducer includes a second inflatable portion associated with the distal end portion of the medical introducer, and the method further comprising inflating the second inflatable portion when the medical introducer is positioned within a patient's body.

62. A method as defined in claim 58, further comprising supplying fluid to the portion of the patient's body through the same medical introducer and visually viewing the produced image from within the portion of the patient's body.

63. A method as defined in claim 58, further comprising conducting a surgical procedure through the steerable working channel device when the steerable working channel device is inserted within the portion of the patient's body.

64. A method as defined in claim 58, wherein the positioning Step includes rotating the imaging device to a selected position and maintaining the position of the imaging device in the selected position without the necessity of a user thereof manually maintaining the position.

65. A method as defined in claim 58, further comprising inserting at least one of the following through the steerable working channel device when inserted within the portion of the patient's body: at least one gamete, at least one sperm, at least one egg, at least one embryo, or at least one blastocyst.

66. A method of performing a medical procedure comprising the steps of:
  positioning an imaging device through a first lumen of a medical introducer positioned within a uterine cavity of a patient's body to thereby produce an image from within the uterine cavity;
  inserting a steerable working channel device through a second lumen of the same medical introducer; and
  inserting at least one of the following through the steerable working channel device when inserted within the uterine cavity: at least one gamete, at least one sperm, at least one egg, at least one embryo, or at least one blastocyst.

67. A method as defined in claim 66, further comprising controlling the steering of the steerable working channel separately and independently from the positioning of the imaging device.

68. A method as defined in claim 67, wherein the positioning step includes rotating the imaging device to a selected position and maintaining the position of the imaging device in the selected position without the necessity of a user thereof manually maintaining the position.

69. A method as defined in claim 68, wherein the imaging device comprises a first imaging device, wherein the steerable working channel device includes an imaging channel, and the method further comprising inserting a second imaging device through the imaging channel of the steerable working channel device when positioned within the medical introducer to also produce an image from within the uterine cavity.

70. A method as defined in claim 66, wherein the medical introducer includes at least a first inflatable portion associated with a distal end portion of the medical introducer, and the method further comprising inflating the first inflatable portion when the medical introducer is positioned within the uterine cavity.

71. A method as defined in claim 70, wherein the medical introducer includes a second inflatable portion associated with the distal end portion of the medical introducer, and the method further comprising inflating the second inflatable portion when the medical introducer is positioned within the uterine cavity.

72. A method as defined in claim 66, further comprising supplying fluid to the uterine cavity through the same medical introducer and visually viewing the produced image from within the uterine cavity.

73. A method of performing a medical procedure comprising the steps of:
   inserting an endoscopic device into a portion of a patient's body;
   inserting a medical introducer having a proximal and distal end portion and a plurality of lumen extending therethrough into the endoscopic device;
   inserting a steerable working channel device through one of the plurality of lumen of the same medical introducer; and
   controlling the steering of the steerable working channel;
   wherein the endoscopic device includes a cannula, and the method further comprising inserting an imaging device through another one of the plurality of lumen of the same medical introducer positioned within the cannula and positioning the imaging device to produce an image from within the portion of the patient's body.

74. A method as defined in claim 73, wherein the steerable working channel device includes an imaging channel, and the method further comprising inserting a second imaging device through the imaging channel of the steerable working channel device when positioned within the medical introducer to also produce an image from within the portion of the patient's body.

75. A method as defined in claim 73, wherein the medical introducer includes at least a first inflatable portion associated with the distal end portion of the medical introducer, and the method further comprising inflating the first inflatable portion when the medical introducer is positioned within the portion of the patient's body.

76. A method as defined in claim 75, wherein the medical introducer includes a second inflatable portion associated with the distal end portion of the medical introducer, and the method further comprising inflating the second inflatable portion when the medical introducer is positioned within a patient's body.

77. A method as defined in claim 73, further comprising supplying fluid to the portion of the body through yet another lumen of the plurality of lumen of the same medical introducer and visually viewing the produced image from within the portion of the patient's body.

78. A method as defined in claim 73, further comprising conducting a surgical procedure through the steerable working channel device when the steerable working channel device is inserted within the portion of the patient's body.

79. A method as defined in claim 73, wherein the positioning step includes rotating the imaging device to a selected position and maintaining the position of the imaging device in the selected position without the necessity of a user thereof manually maintaining the position.

80. A method as defined in claim 73, further comprising inserting at least one of the following through the steerable working channel device when inserted within the portion of the body: at least one gamete, at least one sperm, at least one egg, at least one embryo, or at least one blastocyst.

81. A method of enhancing viewing within a portion of a patient's body comprising the steps of:
   inserting an imaging device through one of a plurality of lumen of a medical introducer positioned within a portion of a patient's body;
   moving the imaging device to a selected position;
   maintaining the position of the imaging device in the selected position without the necessity of a user thereof manually maintaining the position;
   producing an image from within the portion of the patient's body;
   inserting a steerable working channel device through another one of the plurality of lumen of the same medical introducer; and
   controlling the steering of the steerable working channel without moving the position of the imaging device.

82. A method as defined in claim 81, wherein the steerable working channel device includes an imaging channel, and the method further comprising inserting a second imaging device through the imaging channel of the steerable working channel device when positioned within the medical introducer to also produce an image from within the portion of the patient's body.

83. A method as defined in claim 81, wherein the medical introducer includes at least a first inflatable portion associated with a distal end portion of the medical introducer, and the method further comprising inflating the first inflatable portion when the medical introducer is positioned within the portion of the patient's body.

84. A method as defined in claim 83, wherein the medical introducer includes a second inflatable portion associated with the distal end portion of the medical introducer, and the method further comprising inflating the second inflatable portion when the medical introducer is positioned within a patient's body.

85. A method as defined in claim 81, further comprising supplying fluid to the portion of the body through yet another lumen of the plurality of lumen of the same medical introducer and visually viewing the produced image from within the portion of the patient's body.

86. A method as defined in claim 81, further comprising conducting a surgical procedure through the steerable working channel device when the steerable working channel device is inserted within the portion of the patient's body, and wherein the position maintaining step include maintaining the position by use of the medical introducer.

* * * * *

UNITED STATES PATENT AND TRADEMARK OFFICE
CERTIFICATE OF CORRECTION

PATENT NO. : 6,234,958 B1
DATED : May 22, 2001
INVENTOR(S) : Snoke et al.

It is certified that error appears in the above-identified patent and that said Letters Patent is hereby corrected as shown below:

Column 1,
Lines 22-23, please delete "instrumentation has been" and insert -- instrumentation have been -- therefor.

Column 6,
Line 7, delete "since" and insert -- sense -- therefor.

Column 8,
Line 7, delete "provides" and insert -- provide -- therefor.
Line 35, delete "patients" and insert -- patient's -- therefor.
Line 42, delete "advantageous, benefits, and" and insert -- advantageous benefits and -- therefor.

Column 11,
Line 19, delete "medical introducer 3b" and insert -- medical introducer 30 -- therefor.
Line 37, delete "device 30" and insert -- device 80 -- therefor.

Column 12,
Line 42, between "method" and "further", please insert -- can --.

Column 18,
Line 36, delete "an" and insert -- and -- therefor.

Signed and Sealed this

Ninth Day of April, 2002

Attest:

*Attesting Officer*

JAMES E. ROGAN
*Director of the United States Patent and Trademark Office*